Aug. 25, 1964 J. F. DUKE ETAL Plant Pat. 2,439
PEACH TREE
Filed July 30, 1963
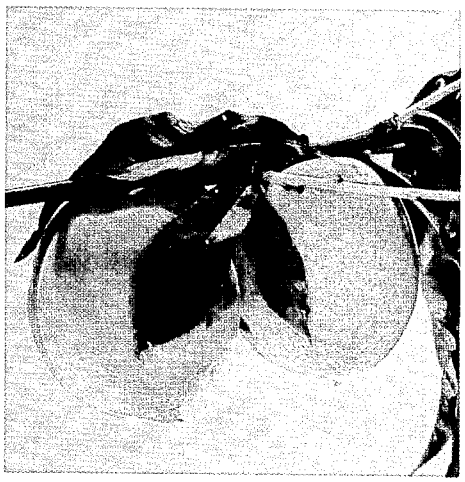
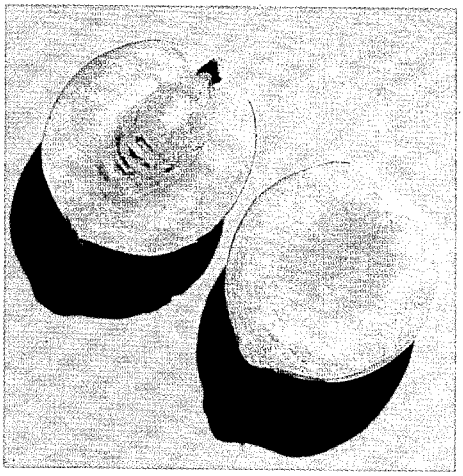
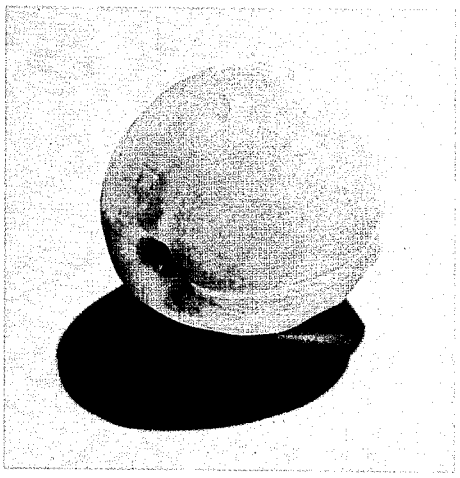
John F. Duke, John F. Duke, Jr.,
AND Leman P. Duke
INVENTORS
By: Jacobi & Dauchow
ATTYS.

United States Patent Office

Plant Pat. 2,439
Patented Aug. 25, 1964

2,439
PEACH TREE

John F. Duke, John F. Duke, Jr., and Leman P. Duke, Fort Valley, Ga., assignors to Charles L. Shepard, Jr., Fort Valley, Ga.

Filed July 30, 1963, Ser. No. 298,810
1 Claim. (Cl. Plt.—43)

The present invention is directed to a new and distinct variety of peach tree which bears yellow-fleshed, semi-freestone fruit.

The new variety disclosed herein is a sport, and finds its origin in the Coronet, an unpatented variety.

A specific advantage offered by the new variety hereof is that it permits the penetration of more distant markets by virtue of its improved shipping qualities over present varieties such as Hiland, an unpatented variety. This results in stabilizing the markets in areas such as the State of Georgia.

A further advantage offered by the new variety hereof is that it is not troublesome with respect to dormancy and thus is more suitable, for example, than the Cardinal, an unpatented variety.

The discovery and development of the new variety was the result of continuous patrolling in our orchards in Crawford County, Georgia for the purpose of achieving an early variety having the flavor, quality, size, eye appeal and shipping endurance of the mid-season and late season varieties. The new variety originated as a limb sport and was discovered by us in 1958 at which time a bud from the new peach tree was grafted into a 3-year old growing Red Cap tree, an unpatented variety. We were successful in getting the new peach tree to come to a true bud. This graft bore fruit in 1960 and has been carefully checked during the years 1960, 1961, 1962 and 1963.

The new variety has been repeatedly, successfully asexually reproduced by bud grafting, and like the aforesaid discovery and development, the asexual reproduction took place in our orchard in Crawford County, Georgia.

The ripening date of the new variety precedes that of the Coronet, an unpatented variety, by two to three weeks, normally 16 days. Moreover, the ripening period of the new variety precedes that of the late season Elberta, an unpatented variety, by approximately seven weeks.

Still further, the new variety has a ripening date which is from two to four days earlier than the present Hiland, an unpatented variety, and the present Cardinal, an unpatented variety.

The characteristics of the new variety are generally the same as those of its parent Coronet, an unpatented variety, except in the following respects:

(*a*) The new variety is approximately ⅛ inch smaller, on average size than the Coronet. (New variety has an average size of 2⅛ inches, whereas Coronet has an average size of 2¼ inches.)

(*b*) The new variety has substantially 70 percent less fuzz than the Coronet. (Coronet variety used as standard 100 percent, whereupon by comparison new variety has approximately 30 percent fuzz.)

(*c*) Hours of dormancy: The new variety has substantially 100 hours more than the Coronet variety, the Coronet variety having 750/950, and the new variety having 850/950.

(*d*) There is a slight difference in body color between the new variety and the Coronet variety, with the new variety occasionally having a lighter red blush.

(*e*) The bottom side color of the new variety is yellow-gold with hues of red flaking, whereas the Coronet variety is yellow-gold. The difference here resides in the flaking.

(*f*) The new variety ripens substantially 16 days before the Coronet variety.

(*g*) The new variety has a superior taste in season to Coronet, and does not deteriorate at maturity as early as Coronet.

The accompanying drawings show typical specimens of the foliage and fruit of our new variety with the upper and lower surfaces of the foliage being illustrated, and with both exterior and sectional views of the fruit being shown, all as depicted in color as nearly true as is reasonably possible in a color illustration of this character.

We claim:

A new and distinct variety of peach tree of the yellow-fleshed, semi-freestone, fruit bearing type, substantially as herein shown and described, characterized particularly as to novelty by the fact that it matures two to three weeks earlier than its parent variety, Coronet, an unpatented variety.

No references cited.